United States Patent
Koh et al.

(10) Patent No.: US 9,903,001 B1
(45) Date of Patent: *Feb. 27, 2018

(54) QUANTITATIVE DETECTION OF PATHOGENS IN CENTRIFUGAL MICROFLUIDIC DISKS

(71) Applicant: National Technology & Engineering Solutions of Sandia, LLC, Albuquerque, NM (US)

(72) Inventors: Chung-Yan Koh, Dublin, CA (US); Ulrich Y. Schaff, Livermore, CA (US); Gregory Jon Sommer, Livermore, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 212 days.

This patent is subject to a terminal disclaimer.

(21) Appl. No.: 13/941,186

(22) Filed: Jul. 12, 2013

Related U.S. Application Data

(60) Provisional application No. 61/673,373, filed on Jul. 19, 2012.

(51) Int. Cl.
  *C12Q 1/68* (2018.01)
(52) U.S. Cl.
  CPC .................................. *C12Q 1/6888* (2013.01)
(58) Field of Classification Search
  None
  See application file for complete search history.

(56) References Cited

U.S. PATENT DOCUMENTS

| | | |
|---|---|---|
| 3,555,284 A | 1/1971 | Anderson |
| 3,744,974 A | 7/1973 | Maddox et al. |
| 4,125,375 A | 11/1978 | Hunter |
| 4,156,570 A | 5/1979 | Wardlaw |
| 4,656,143 A | 4/1987 | Baker et al. |
| 4,683,579 A | 7/1987 | Wardlaw |
| 4,844,818 A | 7/1989 | Smith |
| 5,279,936 A | 1/1994 | Vorpahl |
| 5,635,362 A | 6/1997 | Levine et al. |

(Continued)

FOREIGN PATENT DOCUMENTS

| | | |
|---|---|---|
| WO | WO-2008/143578 | 11/2008 |
| WO | WO-2009/098237 | 8/2009 |

OTHER PUBLICATIONS

Riahi et al. Anal. Chem. 2011. 83(16): 6349-6354 and Supporting Information.*

(Continued)

*Primary Examiner* — Joseph G Dauner
(74) *Attorney, Agent, or Firm* — Blakely, Sokoloff, Taylor & Zafman, LLP

(57) ABSTRACT

A system and methods for detection of a nucleic acid including forming a plurality of nucleic acid detection complexes are described, each of the complexes including a nucleic acid analyte, a detection agent and a functionalized probe. The method further including binding the nucleic acid detection complexes to a plurality of functionalized particles in a fluid sample and separating the functionalized particles having the nucleic acid detection complexes bound thereto from the fluid sample using a density media. The nucleic acid analyte is detected by detecting the detection agent.

9 Claims, 8 Drawing Sheets

(56) References Cited

U.S. PATENT DOCUMENTS

| | | | |
|---|---|---|---|
| 5,639,428 | A | 6/1997 | Cottingham |
| 5,705,628 | A | 1/1998 | Hawkins |
| 5,882,903 | A | 3/1999 | Andrevski et al. |
| 5,892,577 | A | 4/1999 | Gordon |
| 6,153,148 | A | 11/2000 | Thomas |
| 6,319,469 | B1 | 11/2001 | Mian et al. |
| 6,503,722 | B1 | 1/2003 | Valkirs |
| 6,887,384 | B1 | 5/2005 | Frechet et al. |
| 7,033,747 | B2 | 4/2006 | Gordon et al. |
| 7,157,049 | B2 | 1/2007 | Valencia et al. |
| 7,332,326 | B1* | 2/2008 | Kellogg ............. G01N 35/69 422/54 |
| 7,758,810 | B2 | 7/2010 | Lee et al. |
| 2001/0055812 | A1 | 12/2001 | Mian et al. |
| 2002/0098535 | A1 | 7/2002 | Wang et al. |
| 2002/0106786 | A1 | 8/2002 | Carvalho et al. |
| 2002/0137068 | A1 | 9/2002 | Haugland et al. |
| 2002/0151043 | A1 | 10/2002 | Gordon |
| 2002/0164659 | A1 | 11/2002 | Rao et al. |
| 2003/0124719 | A1 | 7/2003 | Woodside |
| 2004/0072278 | A1 | 4/2004 | Chou et al. |
| 2005/0186685 | A1* | 8/2005 | Kange ............. B01F 17/0028 436/180 |
| 2005/0215410 | A1 | 9/2005 | Merino et al. |
| 2005/0282220 | A1 | 12/2005 | Prober et al. |
| 2009/0004059 | A1 | 1/2009 | Pugia et al. |
| 2009/0069554 | A1 | 3/2009 | Finne |
| 2009/0209402 | A1 | 8/2009 | Andersson |
| 2009/0325186 | A1* | 12/2009 | Hinnah et al. ............. 435/7.1 |
| 2010/0068754 | A1 | 3/2010 | Kirakossian |
| 2010/0120596 | A1 | 5/2010 | Froman et al. |
| 2010/0151560 | A1 | 6/2010 | Wo et al. |
| 2011/0045958 | A1 | 2/2011 | Pedrazzini |
| 2013/0260447 | A1 | 10/2013 | Link |
| 2014/0273241 | A1 | 9/2014 | Ochranek et al. |

OTHER PUBLICATIONS

Melting Temperature Calculation. Retrieved on asf from the internet: http://www.biophp.org/minitools/melting_temperature/demo.php?primer=CGT+TAC+CCG+CAG&basic=1&NearestNeighbor=1&cp=200&cs=50&cmg=0.*

Berlier et al. The Journal of Histochemistry and Cytochemistry. 2003. 51(12): 1699-1712.*

Churchill et al. Journal of Microbiological Methods. 2006. 64:141-170.*

PubChem Search results for "2,3-dihydroxypropyl octanoate". Retrieved on Oct. 13, 2016 from the internet: https://www.ncbi.nlm.nih.gov/pccompound/?term=2%2C3-dihydroxypropyl+octanoate.*

Sigma-Aldrich product page for TWEEN 20 archived from Jun. 28, 2012. Retrieved on Oct. 5, 2016 from the internet: https://web.archive.org/web/20120628080753/http://www.sigmaaldrich.com/catalog/product/sial/p1379?lang=en&region=.*

PubChem entry for TWEEN 20. Retrieved on Oct. 4, 2016 from the internet: https://pubchem.ncbi.nlm.nih.gov/compound/Tween_20#section=Names-and-Identifiers.*

Suzuki et al. BMC Genomics. 2007. 8:373.*

Buck et al. BioTechniques. 1999. 27:528-536.*

Abi-Samra, Kameel et al., "Infrared controlled waxes for liquid handling and storage on a CD-microfluidic platform", The Royal Society of Chemistry; Lab on a Chip, 2011, 723-726.

Ahanotu, et al., "Staphylococcal Enterotoxin B as a Biological Weapon: Recognition, Management, and Surveillance of Staphylococcal Enterotoxin", Applied Biosafety; vol. 11 (3), 2006, 120-126.

Albrecht, J.W. et al., "Micro Free-Flow IEF Enhanced Active Cooling and Functionalized Gels", Electrophoresis, 2006, pp. 4960-4969, vol. 27.

Amersham, , "Percoll: Methodology and Applications", 2001, 1-84.

Amukele, et al., "Ricin A-chain activity on stem-loop and unstructured DNA substrates.", Biochemistry; vol. 44(11), Mar. 25, 2005, 4416-4425.

Baldwin, Robert L. , "How Hofmeister Ion Interactions Affect Protein Stability", Biophysical Journal; vol. 71, Oct. 1996, 2056-2063.

Boyko, Matthew et al., "Cell-Free DNA—a Marker to Predict Ischemic Brain Damage in a Rat Stroke Experimental Model", Journal of Neurosurg Anesthesiol, vol. 23, No. 3, Jul. 2011, 222-228.

Brigotti, et al., "Shiga toxin 1 acting on DNA in vitro is a heat-stable enzyme not requiring proteolytic activation", Biochimie Journal; 86(45), 2004, 305-309.

Curtis, R. A. et al., "A Molecular approach to bioseparations: Protein-protein and protein-salt interactions", Chemical Engineering Science; vol. 61, 2006, 907-923.

Endo, et al., "RNA N-Glycosidase Activity of Ricin A-chain. Mechanism of Action of the Toxic Lectin Ricin on Eukaryotic Ribosomes", The Journal of Biological Chemistry, vol. 262, No. 17, Jun. 15, 1987, 8128-8130.

Gorkin, et al., "Centrifugal microfluidics for biomedical applications", www.rsc.org/loc; Lab on a Chip, May 2010, 1758-1773.

Holmberg, et al., "Depurination of A4256 in 28 S rRNA by the Ribosome-inactivating Proteins from Barley and Ricin Results in Different Ribosome Conformations", Journal of Molecular Biology; vol. 259(1), May 31, 1996, 81-94.

Holmes, David et al., "Leukocyte analysis and differentiation using high speed microfluidic single cell impedance cytometry", Lab on a Chip 9, Aug. 7, 2009, 2881-2889.

Huang, et al., "The Primary Structure of Staphylococcal Enterotoxin B. III. The Cyanogen Bromide Peptides of Reduced and Aminoethylated Enterotoxin B, and the Complete Amino Acid Sequence.", The Journal of Biological Chemistry vol. 245 No. 14, Jul. 25, 1970, 3518-3525.

International Search Report and Written Opinion dated Jun. 28, 2013 for PCT/US2013/032349.

Lee, B. S. et al., "A fully automated immunoassay from whole blood on a disc", Lab on a Chip 9, Mar. 5, 2009, 1548-1555.

Lim, C. T. et al., "Bead-based microfluidic immunoassays: The next generation", Biosensors Bioelectronics 22, Jul. 20, 2006, 1197-1204.

Lo, C.T. et al., "Photopolymerized Diffusion-Defined Polyacrylamide Gradient Gels for On-Chip Protein Sizing", The Royal Society of Chemistry, Lab on a Chip, vol. 8, No. 8, 2008, pp. 1273-1279.

Lo, Y. M. D. et al., "Plasma DNA as a Prognostic Marker in Trauma Patients", Clinical Chemistry 46:3, 2000, 319-323.

Madou, Marc et al., "LAB on a CD", Annual Rev. Biomed Eng 8, May 2006, 601-628.

Maes, Melissa L. et al., "Comparison of Sample Fixation and the use of LDS-751 or anti-CD45 or Leukocyte Identification in Mouse Whole Blood for Flow Cytometry", Journal of Immunological Methods, 319(1-2) Jan. 30, 2007, 79-86.

Price, Christopher P. et al., "Light-Scattering Immunoassay", Principles and Practice of Immunoassay (Second Edition); Chapter 18, 1997, 445-480.

Rider, Todd H. et al., "A B Cell-Based Sensor for Rapid Identification of Pathogens", www.sciencemag.org; Science Volume. 301, Jul. 11, 2003, 213-215.

Saukkonen, et al., "Cell-Free Plasma DNA as a Predictor of Outcome in Severe Sepsis and Septic Shock", Clinical Chemistry; vol. 54:6, 2008, 1000-1007.

Schaff, et al., "Whole Blood Immunoassay Based on Centrifugal Bead Sedimentation", Clinical Chemistry Automation and Analytical Techniques 57:5, 2011, 753-761.

Schembri, et al., "Portable Simultaneous Multiple Analyte Whole-Blood Analyzer for Point-of-Care Testing", Clinical Chemistry 38/9, 1992, 1665-1670.

Schneider, et al., "Characterization of EBV-Genome Negative "Null" and "T" Cell Lines Derived from Children With Acute Lymphoblastic Luekemia and Leukemic Transformed Non-Hodgkin Lymphoma", International Journal of Cancer; 19(5), May 15, 1977, 621-626.

(56) References Cited

OTHER PUBLICATIONS

Yu, et al., "Bioinformatic processing to identify single nucleotide polymorphism that potentially affect Ape1 function.", Mutation Research/Genetic Toxicology and Environmental Mutagenesis; vol. 722(2), Jun. 17, 2011, 140-146.
Zhang, L. et al., "A New Biodosimetric Method: Branched DNA-Based Quantitative Detection of B1 DNA in Mouse Plasma", The British Journal of Radiology, vol. 83, Aug. 2010, 694-701.
Ziegler, Annemarie et al., "Circulating DNA: a new diagnostic gold mine?", Cancer Treatment Reviews, vol. 28, 2002, 255-271.
McBain et al., Polyethyleneimine functionalized iron oxide nanoparticles as agents for DNA delivery and transfection, Journal of Materials Chemistry, 17, pp. 2561-2565, available online Apr. 13, 2007.
Andersson, et al., "Parallel nanoliter microfluidic analysis system", Clinical Chemistry, vol. 79, 2007, 4022-4030.
Berry, Scott M., "One-step Purification of Nucleic Acid for Gene Expression Analysis via Immiscible Filtration Assisted by Surface Tension", Lap Chip, 11(10), May 21, 2011, 1747-1753.
Carney, J., "Rapid Diagnostic Tests Employing Latex Particles", Analytical Proceedings, vol. 27, Apr. 1990, 99-100.
Czeiger, David et al., "Measurement of Circulating Cell-Free DNA Levels By A New Simple Fluorescent Test In Patients With Primary Colorectal Cancer", Am J Clin Pathol, vol. 135, 2011, 264-270.
Goldshtein, Hagit et al., "A Rapid Direct Fluorescent Assay for Cell-Free DNA Quantification in Biological Fluids", Annals of Clinical Biochemistry, vol. 46, 2009, 488-494.
Lee, et al., "Fully integrated lab-on-a-disc for simultaneous analysis of biochemistry and immunoassay from whole blood", Lab Chip, vol. 11, 2011, 70-78.
Min, Junhong et al., "Functional Integration of DNA Purification and Concentration Into a Real Time Micro-PCR Chip", The Royal Society of Chemistry; Lab on a Chip, vol. 11, 2011, 259-265.
Rhodes, Andrew et al., "Plasma DNA concentration as a predictor of mortality and sepsis in critically ill patients", Critical Care, vol. 10, No. 2, 2006, 1-7.
Riegger, L. et al., "Read-out concepts for multiplexed bead-based fluorescence immunoassays on centrifugal microfluidic platforms", Sensors and Actuators A-Physical, vol. 126, 2006, 455-462.
Glorikian, Harry et al., "Smart-consumables product development: Implications for molecular diagnostics", DX Directions, Spring 2010, 12-16.
Gusev et al., "Capillary columns with in situ formed porous monolithic packing for micro high-performance liquid chromatography and capillary electrochromatography", Journal of Chromatography A, 1999, vol. 855(1), pp. 273-290.
Huang et al., "The primary structure of Staphylococcal enterotoxin B: III. The cyanogen bromide peptides of reduced and aminoethylated enterotoxin B, and the complete amino acid sequence", Journal of Biological Chemistry, 1970, vol. 245(14), pp. 3518-3525.
IVD Technology, "Microfluidic applications for IVDs", DX Directions, 2010, Spring, pp. 1-26.
Kim et al., "Fully integrated lab-on-a-disc for nucleic acid analysis of food-borne pathogens", Analytical Chemistry, 2014, vol. 86, pp. 3841-3848.
Koh et al., "Centrifugal microfluidic platform for ultrasensitive detection of botulinum toxin", Analytical Chemistry, 2015, vol. 81, pp. 922-928.

\* cited by examiner

QUANTITATIVE DETECTION OF PATHOGENS IN CENTRIFUGAL MICROFLUIDIC DISKS

CROSS-REFERENCE TO RELATED APPLICATIONS

The application claims the benefit of the earlier filing date of U.S. Provisional Patent Application No. 61/673,373, filed Jul. 19, 2012 and incorporated herein by reference.

GOVERNMENT RIGHTS

This invention was made with Government support under Contract No. DE-AC04-94AL85000 awarded by the U.S. Department of Energy. The Government has certain rights in the invention.

FIELD OF THE INVENTION

The present invention relates in general to detection of a target analyte using a microfluidic disk, more specifically detection of a nucleic acid analyte using a microfluidic disk. Other embodiments are also described and claimed.

BACKGROUND

Sandwich assays generally proceed by adsorbing a target analyte onto a surface coated with a capture agent. The target analyte is then detected using a detection agent that also binds to the target analyte at a different site than the capture agent. Signal from the detection agent is used to detect the target analyte. For example, a substrate may include a number of capture agents on its surface. A fluid sample including detection agents and target analyte are introduced to the surface. The target analyte binds to the capture agent. The detection agent also binds to the target analyte. In this manner, complexes including a capture agent, a target analyte, and a capture agent may be formed on the substrate. Some free detection agent may remain in the fluid sample and is not involved in a complex. The free detection agent is not representative of the presence of target analyte, because it is not bound to the target analyte. That is, the unbound detection agent may generate a false positive signal indicating the presence of the target analyte. Accordingly, the signal from the free detection agent may obscure accurate detection. Accordingly, multiple wash steps are performed to rinse away the free detection agent, leaving only complexed detection agents bound to a target analyte remaining on the substrate.

The detectable signal from the detection agent bound to the substrate, however, may be too low for accurate detection. For example, the complexed detection agent may be spread across too large an area of the substrate to generate sufficient signal for detection. Accordingly, additional labeling agents may be added and may bind to the complexes to increase the amount of signal generated by the complexes.

In the case of a target analyte such as a bacterial pathogen or other nucleic acid analyte, the detection process can take several days and require a highly trained specialist to examine the morphology and phenotype of the bacteria. In addition, although molecular biology techniques such as Southern blots, Western blots, and PCR have been adapted for clinical use, these techniques require amplification of the signal through thermocycling and secondary antibodies, thereby causing further delay.

SUMMARY

An embodiment of the invention includes forming a nucleic acid detection complex from a DNA probe synthesized against a desired DNA analyte. Representatively, in one embodiment, the DNA probe may be a biotinylated, double-stranded, quenched-FRET DNA probe synthesized against a pathogen such as 16S ribosomal RNA of *E. coli* or the listeriolysin O gene of *L. monocytogenes*. The unreacted probe may include a donor strand having a detection agent and a quencher strand having a quencher agent. The quencher agent may have an absorbance with a significant spectral overlap to that of the detection agent such that when the strands are together, no signal is detected. The quencher agent may be attached to the 3' end of the quencher strand, which is complementary to the donor strand, but significantly shorter. The detection agent may be attached to the 5' end of a donor strand complementary to a region of the target analyte. A mixture of the probe and target analyte may be heated to a temperature sufficient to cause the quencher strand to melt off of the donor strand. The donor strand then serves as an active probe which is free to hybridize with the complementary strand of the target analyte. When the temperature is lowered again, any donor strands which lack the target analyte will hybridize back to the quencher strand, preventing any false fluorescent signals from being detected. If there is target analyte hybridized to the donor strand, the detection agent can be detected. The donor strand may also be functionalized with a binding agent to facilitate binding of the donor strand to a desired carrier.

This nucleic acid detection complex (e.g., donor strand, target analyte and functionalized probe strand) may be bound to the carrier in a fluid sample. In one embodiment, the carrier may be a silica particle. The particle having the nucleic acid detection complex bound thereto may then be separated from the fluid sample using a density media. The density media may be held within a chamber of a microfluidic disk which spins to create a centrifugal force which drives the particles having the complex bound thereto through it, without the sample media, to form a pellet. A detection module may then be used to detect a signal from the detection agent within the pellet. Since the detection agent is bound to the target analyte, the signal from the detection agent can be used to quantify the target analyte.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one.

DETAILED DESCRIPTION

In this section we shall explain several preferred embodiments of this invention with reference to the appended drawings. Whenever the shapes, relative positions and other aspects of the parts described in the embodiments are not clearly defined, the scope of the invention is not limited only to the parts shown, which are meant merely for the purpose of illustration. Also, while numerous details are set forth, it is understood that some embodiments of the invention may be practiced without these details. In other instances, well-known structures and techniques have not been shown in detail so as not to obscure the understanding of this description.

Figure 1:
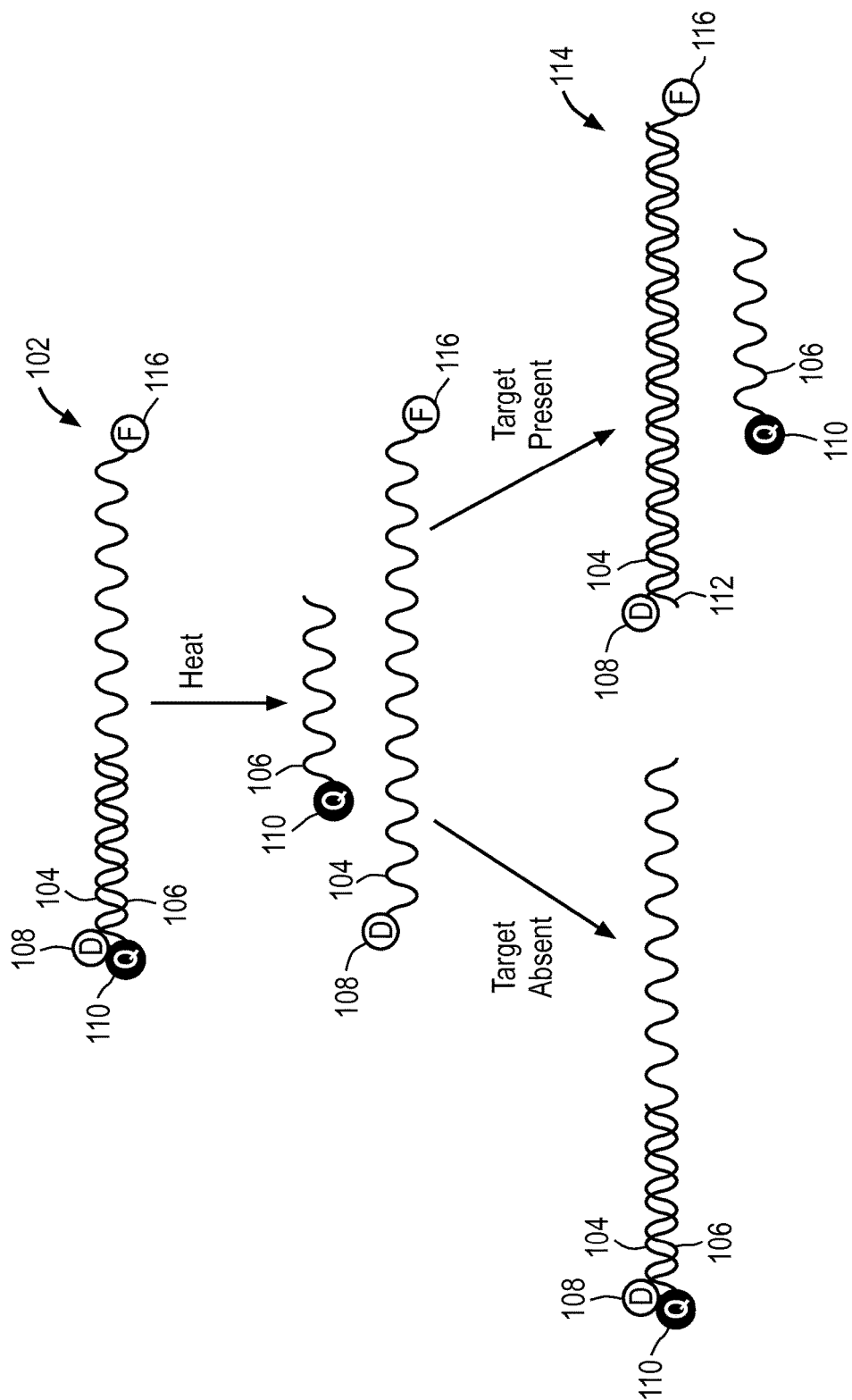
FIG. 1 shows a flow diagram illustrating one embodiment of a method for forming a nucleic acid detection complex.

FIG. 1 shows a flow diagram illustrating one embodiment of a method for forming a nucleic acid detection complex. In one embodiment, the nucleic acid detection complex 114 is formed from an unreacted probe 102 which may include a reactive probe component capable of binding to a target analyte. Representatively, in one embodiment, unreacted probe 102 is a double-stranded, quenched Förster (fluorescence) resonance energy transfer (FRET) probe. In this aspect, unreacted probe 102 may have complementary DNA strands such as donor strand 104 and quencher strand 106. Donor strand 104 may have bound thereto one or more of a detection agent 108 and quencher strand 106 may have one or more of a quencher agent 110. The detection agent 108 and quencher agent 110 may be fluorophore dyes which can re-emit light upon light excitation. Representatively, in one embodiment, detection agent 108 may be an AlexaFluor 647 fluorescent dye having a maximum emission of 670 nanometers (nm). Quencher agent 110 may be an Iowa Black® RQ fluorescent dye having a maximum absorbance of 667 nm, thus providing a significant spectral overlap and high FRET efficiency with the detection agent 108.

In one embodiment, detection agent 108 may be attached to the 5' end of donor strand 104. Quencher agent 110 may be attached to the 3' end of quencher strand 106. Donor strand 104 may be longer than quencher strand 106. For example, donor strand 104 may be a 25 or more base strand, while quencher strand 106 has less than 25 base pairs, for example, 12 base pairs. Donor strand 104 may be a DNA strand complementary to the target analyte. For example, in one embodiment, donor strand 104 is complementary to a nucleic acid analyte such as DNA or rRNA. In one embodiment, the DNA may be a synthetic DNA target. For example, the nucleic acid analyte may be a pathogen such as 16S ribosomal RNA of E. coli or the listeriolysin O gene of L. monocytogenes. Under the appropriate conditions, as will be described below, the target analyte can hybridize to donor strand 104. Thus, donor strand 104 may be considered the active probe component of unreacted probe 102.

At room temperature donor strand 104 and quencher strand 106 are bound together. When donor strand 104 and quencher strand 106 are bound together, detection agent 108 does not emit light because it is "quenched" by quencher agent 110. In other words, the excitation energy of detection agent 108, which would normally cause it to emit light, is transferred to quencher agent 110. When unreacted probe 102 is heated, however, quencher strand 106 will melt away from donor strand 104. Unreacted probe 102 can be heated to a temperature sufficient to cause removal of quencher strand 106 from donor strand 104, but which is less than a melting temperature of the target analyte 112. For example, in the case where the target analyte is 16S rRNA of E. coli, unreacted probe 102 is heated to a temperature of at least 45 degrees Celsius (C) (the melting temperature of probe 102) but less than 75 degrees C. (the melting temperature of 16S rRNA of E. coli), for example, about 65 degrees C. Thus, at 65 degrees C., in the presence of the target analyte 112, quencher strand 106 will melt off of donor strand 104 and be thermodynamically displaced by the target analyte 112 as illustrated in FIG. 1. Any donor strand hybridized with a target analyte will emit a detectable light signal since the quencher is no longer within FRET distance. When the temperature is lowered, for example to 25 degrees C., any donor strand lacking the target will re-hybridize with a quencher strand, preventing any fluorescent signals from donor strands not bound to a target analyte.

In some embodiments, donor strand 104 may include a functional agent 116 to facilitate binding of donor strand 104 (and any target analyte hybridized thereto) to a carrier as will be described in more detail in reference to FIG. 2A-2C. Functional agent 116 may therefore be any type of binding molecule which is complementary to that of the carrier such as a protein binding agent, antibody binding agent or a nucleic acid binding agent. Representatively, in one embodiment, donor strand 104 may be biotinylated with a biotin functional agent 116 such that it is capable of binding with a carrier having an avidin or streptavidin functional component.

Thus, in one embodiment, nucleic acid detection complex 114 includes donor strand 104 having functional agent 116 bound thereto (also referred to herein as a functionalized probe), detection agent 108 and target analyte 112 as illustrated in FIG. 1. In some embodiments, to facilitate detection of a signal from detection agent 108, it may be desirable to concentrate a plurality of nucleic acid detection complexes 114 about a carrier. Particularly where the target analyte is to be detected using a microfluidic disk.

Figure 2A:
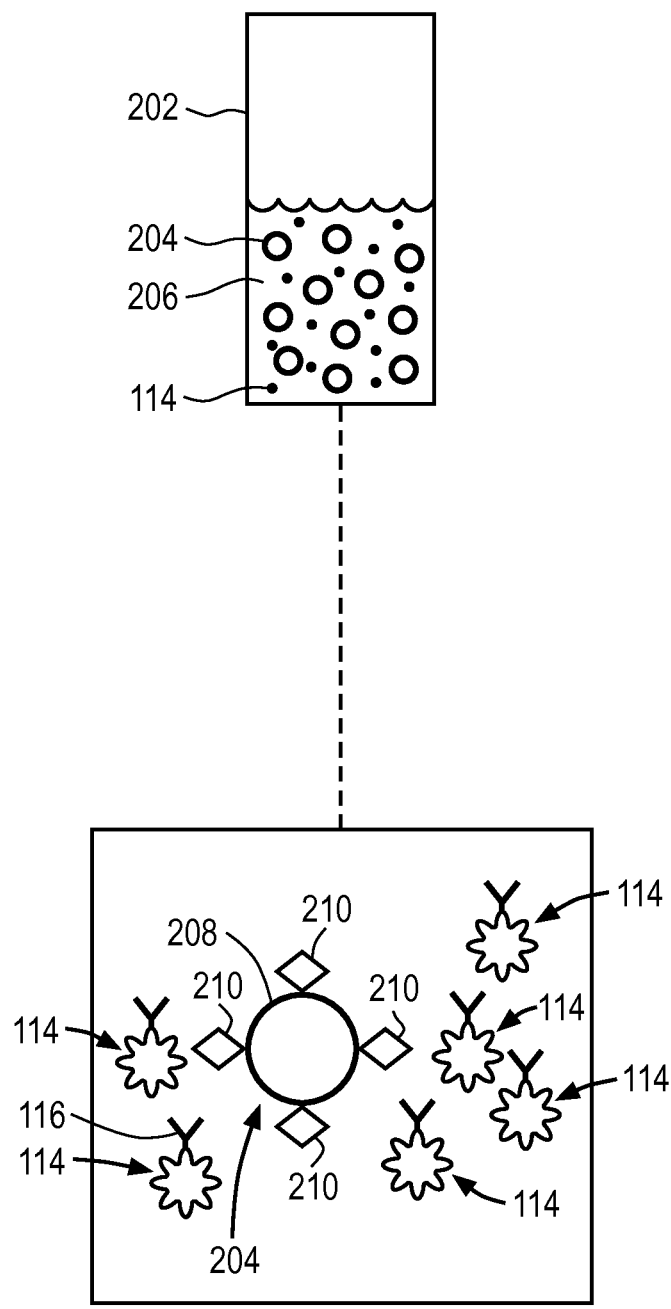
FIG. 2A illustrates one embodiment of a process for binding a plurality of nucleic acid detection complexes to a carrier.
Figure 2B:
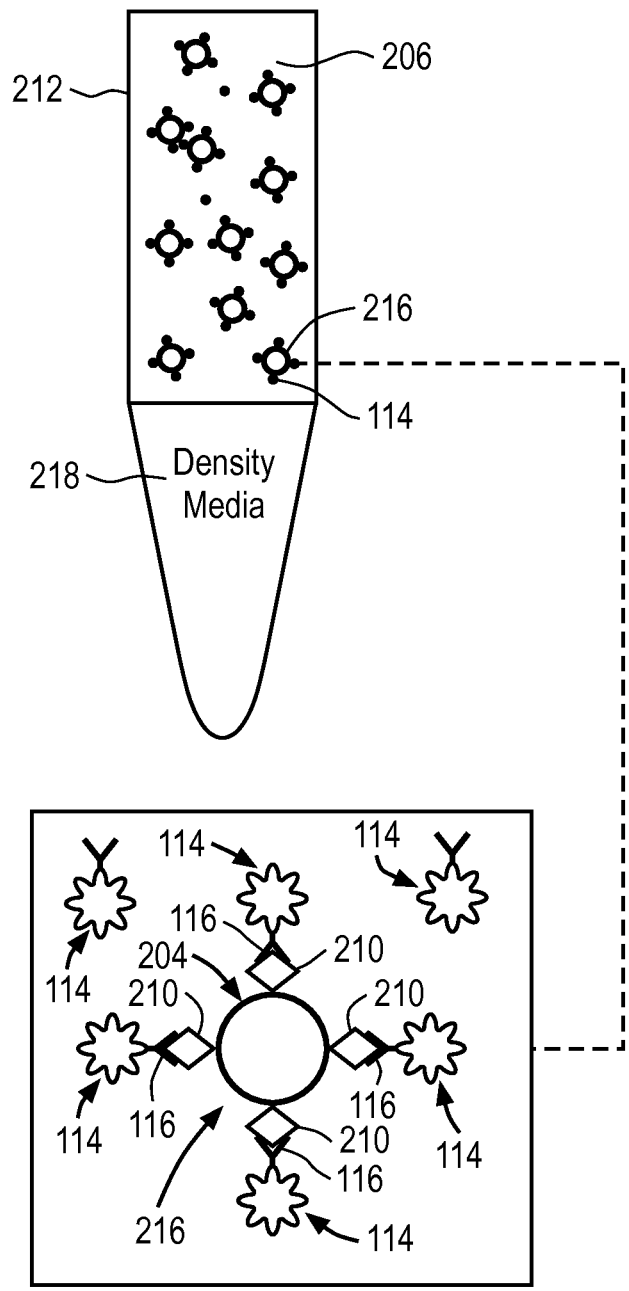
FIG. 2B illustrates one embodiment of a process for binding a plurality of nucleic acid detection complexes to a carrier.
Figure 2C:
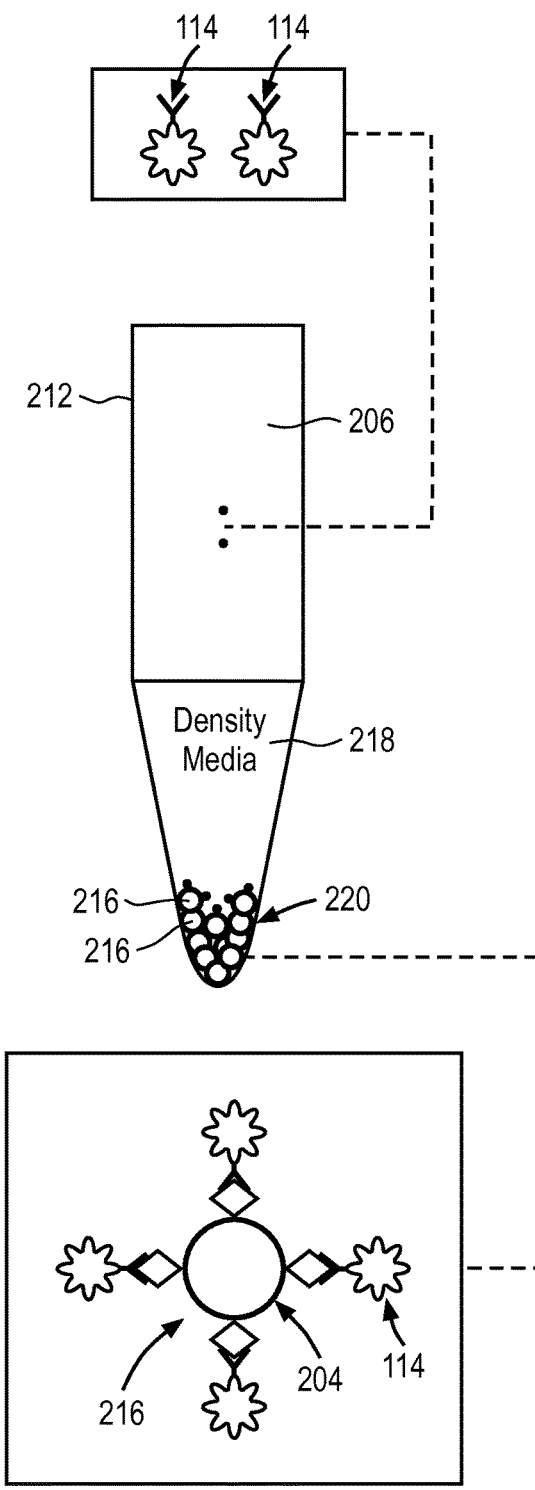
FIG. 2C illustrates one embodiment of a process for binding a plurality of nucleic acid detection complexes to a carrier.

FIG. 2A-FIG. 2C illustrate a process for binding a plurality of nucleic acid detection complexes to a carrier. In one embodiment, the carrier 204 may be a particle 208 suitable for conducting a detection assay as described herein. Representatively, in one embodiment, particle 208 may be, but is not limited to, a polystyrene particle or silica particle. Substantially any particle radii may be used. Exemplary particles may include particles having a radius ranging from 150 nanometers to 3 microns. In other examples, the particles may have a diameter of between 0.15 and 10 microns. Other sizes may also be used.

Particle 208 may have one or more of a functional agent 210 bound thereto. The functional agent 210 may be complimentary to that of nucleic acid detection complex 114 such that nucleic acid detection complexes 114 may be bound to particle 208. Functional agent 210 may be any type of agent suitable for binding to the functional agent 116 of nucleic acid detection complex 114, for example, a protein binding agent, antibody binding agent or a nucleic acid binding agent. Representatively, functional agent 210 may be, but is not limited to, avidin or streptavidin.

In some embodiments, the nucleic acid detection complex 114 may be bound to carrier 204 in a fluid sample 206. The fluid sample 206 may be any type of fluid media that is biologically compatible with nucleic acid detection complexes 114 and carriers 204. For example, fluid sample 206 may be a buffer solution or other biological solution within which the nucleic acid detection complex 114 was formed. Fluid sample 206 having carriers 204 and unbound nucleic acid detection complexes 114 therein may be placed within a mixing chamber 202. In some embodiments, the mixing chamber 202 may be part of a microfluidic disk, as will be described in more detail in reference to FIG. 4 and FIG. 5.

As can be seen from the magnified view of FIG. 2A, each carrier 204 within fluid sample 206 includes a plurality of functional agents 210 (e.g., streptavidin) bound to a surface of particle 208. Functional agents 210 are complimentary to the functional agent 116 bound to each nucleic acid detection complex 114. Therefore upon incubation of the carrier 204 with the nucleic acid detection complex 114, the functional agent 116 of the nucleic acid detection complex 114 binds to a functional agent 210 of particle 208 to form a concentrated detection particle 216 as illustrated by FIG. 2B. In some embodiments, fluid sample 206 may be transferred from the mixing chamber 202 to a detection chamber 212 prior to incubation and incubated within the detection chamber 212. Alternatively, incubation may occur within the mixing chamber 202.

Detection chamber 212 may include a density media 218 that facilitates separation of the concentrated detection particle 216 (which includes particle 204 having the nucleic acid detection complex 114 bound thereto) from fluid sample 206. The density media 218 may be any type of density media that is less dense than the concentrated detection particle 216, but more dense than the fluid sample 206. An example of a suitable density media is Percoll®, available from GE Lifesciences. Particular densities may be achieved by adjusting a percentage of Percoll® in the salt solution. More generally, viscosity and density may be adjusted by changing a composition of the media. Varying the concentration of solutes such as, but not limited to, sucrose or dextran, in the density media, may adjust the density and/or viscosity of the media. In some embodiments, the density media may include a detergent, such as Tween® 20. The detergent may enhance a wash function of transport through the density media, as will be described further below. Representatively, in one embodiment, the density media may include a seven percent dextran dissolved in a physiological salt solution containing 0.05% Tween® 20. The density of this example density media is 1.025 specific gravity.

To drive the concentrated fluid detection particle 216 through density media 218, the microfluidic disk within which the detection chamber 212 is formed may be spun creating a centrifugal force that drives the sample toward density media 218. The concentrated fluid detection particle 216, which has a greater density than density media 218, is forced through density media 218 while fluid sample 206 remains outside of density media 218 as illustrated by FIG. 2C. Representatively, in one embodiment, the microfluidic disk is spun at 8000 RPM for approximately 10 minutes to introduce each concentrated fluid detection particle 216 to the density media, and transport each concentrated fluid detection particle 216 through the density media 218. Everything that does not bind to carriers 204 (e.g. unbound complexes 114, unbound quencher strands 106 and rehybridized probes) will remain within fluid sample 206, outside of density media 218.

The concentrated fluid detection particles 216 may form a pellet 220 at the bottom of detection chamber 212. The fluorescent intensity of the concentrated fluid detection particles 216 within pellet 220 may be detected by fluorescence microscopy, for example, using a Cy5 filter and mercury lamp excitation.

Figure 3:
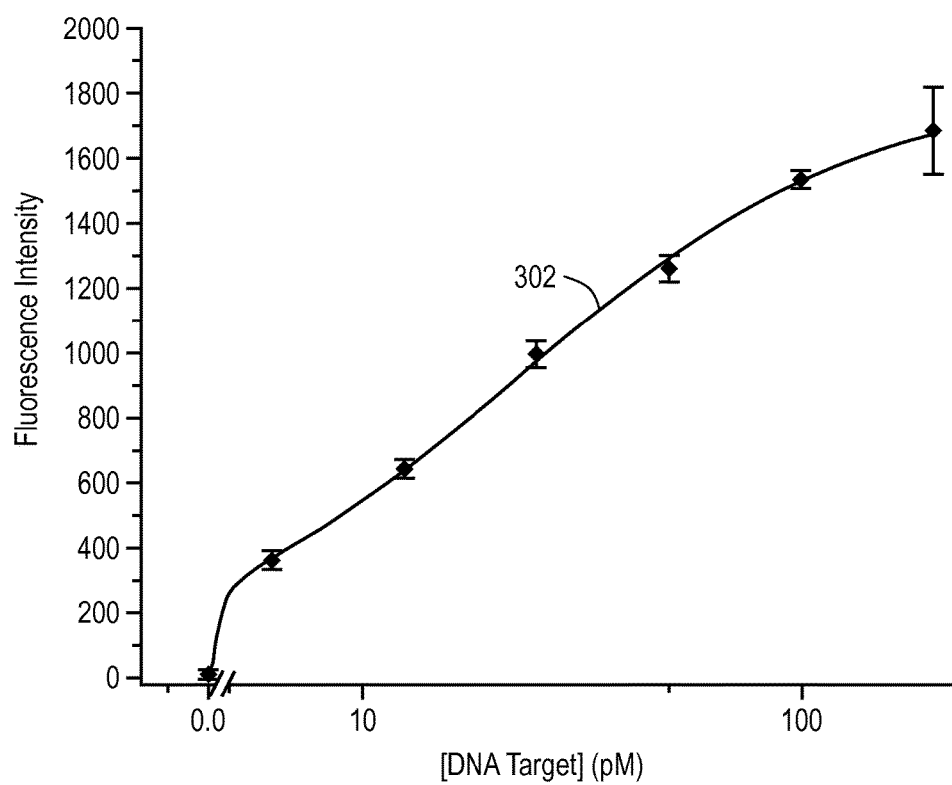
FIG. 3 illustrates one embodiment of a dose response curve for detection of a nucleic acid analyte using a quenched probe system.

An average fluorescence intensity may be plotted and displayed as illustrated by FIG. 3. Representatively, FIG. 3 illustrates one embodiment of a dose response curve for detection of a synthetic DNA target analyte using the quenched-FRET probe system described herein. As illustrated by curve 302, the limit of detection is 2 pM and the limit of quantification is 5 pM. The standard deviation is illustrated by the vertical error bars.

Figure 4:
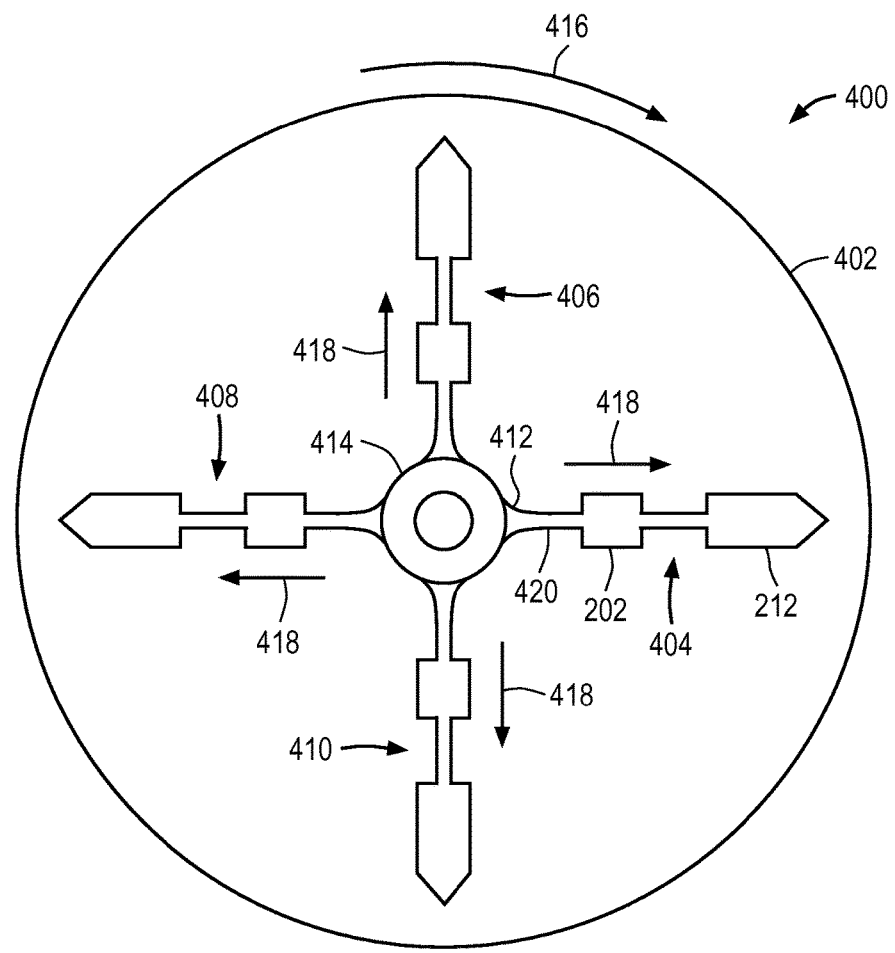
FIG. 4 shows a schematic illustration of one embodiment of a microfluidic disk.

One exemplary embodiment of a microfluidic disk will now be described in reference to FIG. 4. In one embodiment, microfluidic disk 400 may include a substrate 402 which may at least partially define regions of assay areas 404, 406, 408 and 410. The microfluidic disk 400 may include a fluid inlet port 414 in fluid communication with the assay areas 404, 406, 408 and 410. During operation, as will be described further below, fluids including fluid samples, density media, and/or particles suspended in a fluid, may be transported using centrifugal force from an interior of the microfluidic disk 400 toward a periphery of the microfluidic disk 400 in a direction indicated by an arrow 418. The centrifugal force may be generated by rotating the microfluidic disk 400 in the direction indicated by the arrow 416, or in the opposite direction.

The substrate 402 may be formed using any of a variety of suitable substrate materials. In some embodiments, the substrate may be a solid transparent material. Transparent plastics, quartz, glass, fused-silica, PDMS, and other transparent substrates may be desired in some embodiments to allow optical observation of samples within the channels and chambers of the disk 400. In some embodiments, however, opaque plastic, metal or semiconductor substrates may be used. In some embodiments, multiple materials may be used to implement the substrate 402. The substrate 402 may include surface treatments or other coatings, which may, in some embodiments, enhance compatibility with fluids placed on the substrate 402. In some embodiments surface treatments or other coatings may be provided to control fluid interaction with the substrate 402. While shown as a round disk in FIG. 4, the substrate 402 may take substantially any shape, including a square shape.

In some embodiments, as will be described further below, the substrate 402 may itself be coupled to a motor for rotation. In some embodiments, the substrate may be mounted on another substrate or base for rotation. For example, a microfluidic chip fabricated at least partially in a substrate may be mounted on another substrate for spinning. In some examples, the microfluidic chip may be disposable while the substrate or base it is mounted on may be reusable. In some examples, the entire disk may be disposable. In some examples, a disposable cartridge including one or more microfluidic channels may be inserted into the disk or other mechanical rotor that forms part of a detection system.

The substrate 402 may generally, at least partially, define a variety of fluidic features. The fluidic features may be microfluidic features. Generally, microfluidic, as used herein, refers to a system, device, or feature having a dimension of around 1 mm or less and suitable for at least partially containing a fluid. In some embodiments, 500 microns or less. In some embodiments, the microfluidic features may have a dimension of around 100 microns or less. Other dimensions may also be suitable depending upon the desired application. The fluidic features may include any number of channels, chambers, inlet/outlet ports, or other features.

Microscale fabrication techniques, generally known in the art, may be utilized to fabricate the microfluidic disk 400. The microscale fabrication techniques employed to fabricate the microfluidic disk 400 may include, for example, embossing, etching, injection molding, surface treatments, photolithography, bonding and other techniques.

A fluid inlet port 414 may be provided to receive a fluid that may be analyzed using the microfluidic disk 400. The fluid inlet port 414 may have generally any configuration, and a fluid sample may enter the fluid inlet port 414 utilizing substantially any fluid transport mechanism, including pipetting, pumping, or capillary action. The fluid inlet port 414 may take substantially any shape. Generally, the fluid inlet port 414 is in fluid communication with at least one or more of assay areas 404, 406, 408 and 410. Generally, by fluid communication it is meant that a fluid may flow from one area to the other, either freely or using one or more transport forces and/or valves, and with or without flowing through intervening structures.

The assay area 404 will now be described further below, and generally may include one or more channels in fluid communication with the fluid inlet port 414. It is to be understood that each of assay areas 404, 406, 408 and 410 may be substantially similar therefore the description of assay area 404 provided herein should be understood as applying to assay areas 406, 408 and 410. Although four assay areas 404, 406, 408, 410 are shown in FIG. 4, generally any number may be present on the microfluidic disk 400.

As the microfluidic disk 400 is rotated in the direction indicated by the arrow 416 (or in the opposite direction), a centrifugal force may be generated. The centrifugal force may generally transport fluid from the inlet port 414 into one or more of the assay areas 404-410. Assay area 404 may include a mixing chamber 202 and a detection chamber 212 as previously discussed. Each of mixing chamber 202 and detection chamber 212 may be in fluid communication with fluid inlet port 414 via channel 420. The mixing chamber 202 and detection chamber 212 may generally be of any size and shape, and may contain one or more reagents including solids and/or fluids which may interact with fluid entering and/or exiting the features.

The mixing chamber 202 may be a channel or chamber configured to contain a fluid sample and any agents to be mixed (e.g., a nucleic acid analyte 112, FRET unreacted probe 102 and carrier 204). The detection chamber 202 may be configured to contain a density media as previously discussed in reference to FIGS. 2B-2C.

The detection chamber 202 may be a channel or chamber generally configured to allow for separation of agents and/or particles from the fluid sample contained therein and detection of a signal emitted by labeling agents within the nucleic acid detection complex. As will be described further below, centrifugal forces may generally be used to transport a fluid sample including nucleic acid detection complexes and/or particles from the fluid inlet port 414 and/or mixing chamber 202 toward the detection chamber 212. Additionally, in some embodiments, microfluidic disk may include a separate chamber for the density media, which is in fluid communication with detection chamber 212. Centrifugal forces may be used to transport density media from the separate density media chamber to the detection chamber 212.

Microfluidic disk 400 may be used to detect nucleic acid target analyte 112, as described in reference to FIG. 1, as follows. Representatively, in one embodiment, unreacted probe 102 may be mixed with target analyte 112, for example, in a fluid sample such as a buffer solution. The mixture may be introduced into fluid inlet port 414 of microfluidic disk 400 and pass to mixing chamber 202 via channel 420. The mixture may then be heated by a heating component within disk 400 to separate the donor strand 104 from the quencher strand 106 of the unreacted probe 102. Alternatively, the mixture may be heated prior to introducing the mixture to microfluidic disk 400 for processing. The target analyte 112 then hybridizes to the separated donor strand 104 to form the nucleic acid detection complex 114. In some embodiments, the mixture is cooled to facilitate rehybridization of the unbound quencher strand 106 to any unbound donor strands. 104 and/or hybridization of the target analyte 112 to the separated donor strand 104. Cooling may occur using a cooling component within microfluidic disk 400, or by another cooling feature prior to adding the mixture to the microfluidic disk 400. Once one or more of nucleic acid detection complex 114 is formed, carriers 204 may be introduced into mixing chamber 202. For example, carriers 204 may be introduced into microfluidic disk 400 through fluid inlet port 414 and transported to mixing chamber 202 through channel 420. Once carriers 204 and one or more of nucleic acid detection complex 114 are mixed together, the functional binding agents associated with each, cause one or more of nucleic acid detection complex 114 to bind to the carriers 204, in some embodiments particles 208, forming concentrated detection particles 216 within the fluid sample. The sample, having concentrated detection particles 216 therein is then transported to detection chamber 212 via channel 420, such as by a centrifugal force caused by spinning of microfluidic disk 400. An additional centrifugal force is then applied to drive concentrated detection particles 216 through the density media within detection chamber 212 and form a pellet 220. Fluorescent signals from the detection agents within the detection particles 216 may be detected by a detection module in order to detect and/or quantify the nucleic acid target analyte 112 associated therewith.

Figure 5:
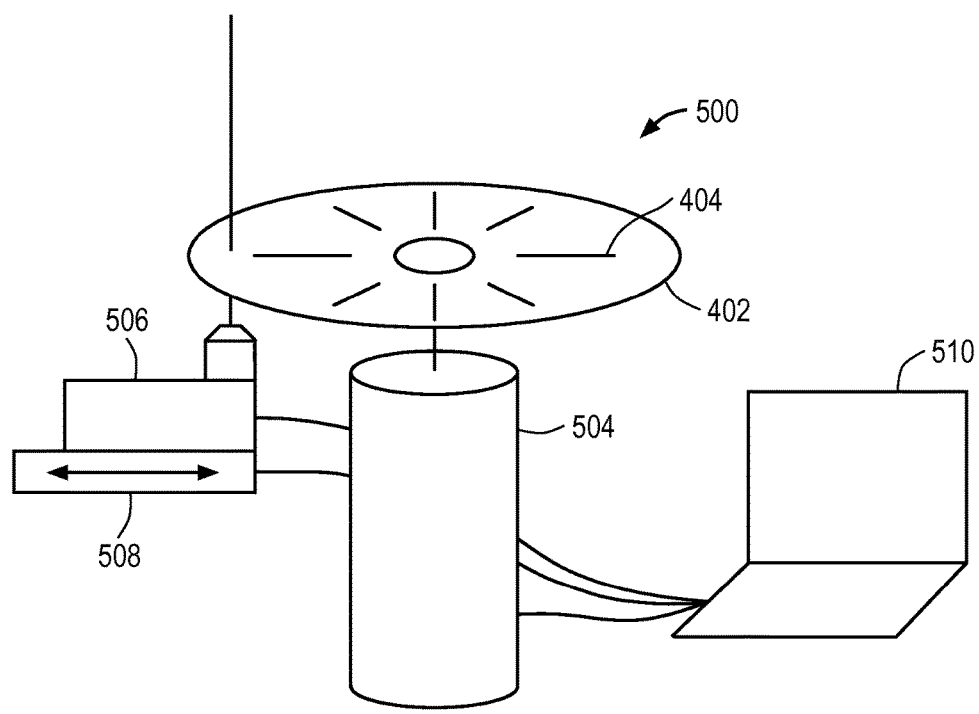
FIG. 5 shows a schematic illustration of one embodiment of a system for detection of a nucleic acid analyte.

FIG. 5 is a schematic illustration of a system according to an embodiment of the present invention. The system 500 may include the microfluidic disk 400 of FIG. 4 with one or more assay areas 404. A motor 504 may be coupled to the disk 400 and configured to spin the microfluidic disk 400, generating centrifugal forces. A detection module 506 may be positioned to detect signal from labeling agents in a detection region of the assay area 404, as will be described further below. An actuator 508 may be coupled to the detection module 506 and configured to move the detection module along the detection region in some examples. A processing device 510 may be coupled to the motor 504, the detection module 506, and/or the actuator 508 and may provide control signals to those components. The processing device 510 may further receive electronic signals from the detection module 506 corresponding to the labeling agent signals received by the detection module 506. All or selected components shown in FIG. 5 may be housed in a common housing in some examples. Microfluidic disks, which may be disposable, may be placed on the motor 504 and removed, such that multiple disks may be analyzed by the system 500. The motor 504 may be implemented using a centrifugation and/or stepper motor.

The motor 504 may be positioned relative to the detection module 506 such that, when the microfluidic disk 400 is situated on the motor 504, the disk is positioned such that a detection region of the assay area 404 is exposed to the detection module 506. The detection module 506 may include a detector suitable for detecting signal from detection agents in complexes including at least one nucleic acid analyte, a functional agent and the detection agent. The complexes may be formed on the surface of one or more particles, as previously discussed. The detector may include, for example, a laser and optics suitable for optical detection of fluorescence from fluorescent labeling agents. The detection module may include one or more photomultiplier tubes. In other examples, other detectors, such as electronic detectors or CCD cameras, may be used. The actuator 508 may move the detector in some examples where signal may be detected from a variety of locations of the microfluidic disk 400, as will be described further below.

The processing device 510 may include one or more processing units, such as one or more processors. In some examples, the processing device 510 may include a controller, logic circuitry, and/or software for performing functionalities described herein. The processing device 510 may be coupled to one or more memories, input devices, and/or output devices including, but not limited to, disk drives, keyboards, mice, and displays. The processing device 510 may provide control signals to the motor 504 to rotate the microfluidic disk 400 at selected speeds for selected times, as will be described further below. The processing device 510 may provide control signals to the detection module 506, including one or more detectors and/or actuators, to detect signals from the label moieties and/or move the detector to particular locations, as will be described further below. The processing device 510 may develop these control signals in accordance with input from an operator and/or in accordance with software including instructions encoded in one or more memories, where the instructions, when executed by one or more processing units, may cause the processing device to output a predetermined sequence of control signals. The processing device 510 may receive electronic signals from the detection module 506 indicative of the detected signal from detection agents. The processing device 510 may detect a target analyte and/or calculate a quantity of a target analyte in a pellet based on the signals received from the detection module 506, as will be described further below. Accordingly, the processing device 510 may perform calculations as will be described further below. The calculations may be performed in accordance with software including one or more executable instructions stored on a memory causing the processing device to perform the calculations. Results may be stored in memory, communicated over a network, and/or displayed. It is to be understood that the configuration of the processing device 510 and related components may vary, and any of a variety of computing systems may be used including server systems, desktops, laptops, hand held devices such as tablet computers, controllers, and the like.

Having described examples of microfluidic disks and systems, some discussion will now be provided regarding mechanisms for separation and centrifugation of the sample. The discussion regarding mechanisms is provided as an aid to understanding examples of the present invention, but is in no way intended to limit embodiments of the present invention. That is, embodiments of the present invention may not employ the described mechanisms. Sedimentation of particles may occur within a viscous fluid under the influence of gravitational field (which may be natural or induced by centrifugation). For nanometer scale particles, such as proteins or nucleic acids, however, gravitational forces will generally not cause motion of these nanometer scale particles over significant distances during typical centrifugal conditions (<100,000 g). Accordingly, the nucleic acid detection complexes, which are relatively small molecules, are bound to larger carriers (e.g., carriers 204) using binding agents. By forming complexes on the particles, and separating the particles from the remaining sample using centrifugal forces, the need for wash steps may be reduced or eliminated, because unbound detection agents and/or other molecules may be dissociated from the particles by fluid flow.

Figure 6:
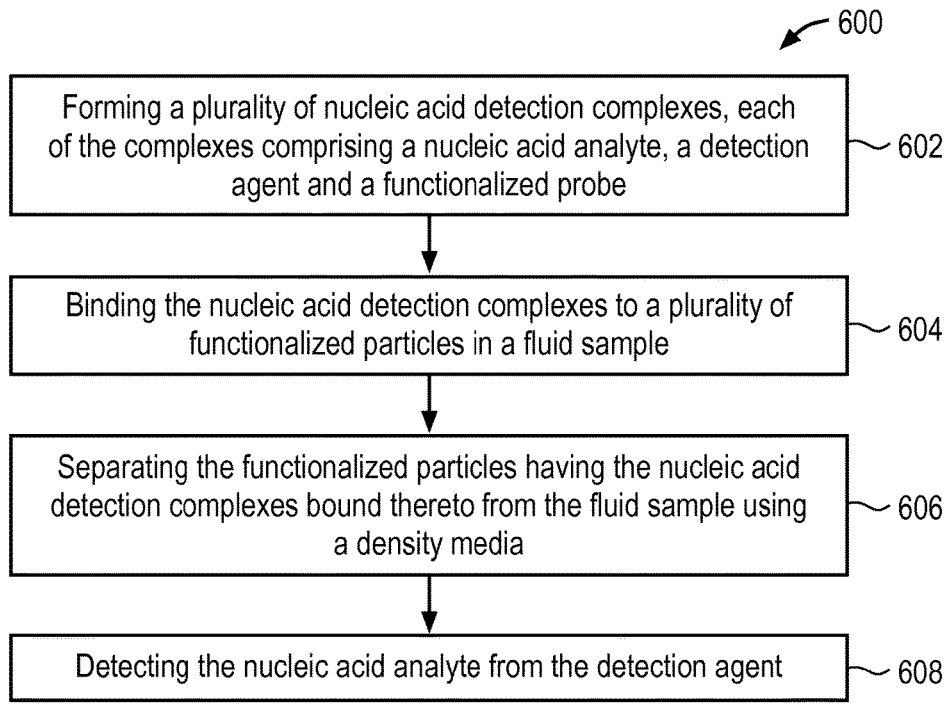
FIG. 6 illustrates a flow diagram of one embodiment of a process for detecting a nucleic acid analyte.

FIG. 6 illustrates a flow diagram of one embodiment of a process for detecting a nucleic acid analyte. Representatively, in one embodiment, process 600 includes forming a plurality of nucleic acid detection complexes having a nucleic acid analyte, a detection agent and a functionalized probe (block 602). The nucleic acid detection complex may be formed by an incubation step prior to or within an associated microfluidic disk. For example, the microfluidic disk may have a heating or cooling component formed thereon which can heat a mixture containing the nucleic acid analyte, detection agent and functionalized probe to a hybridization temperature sufficient to cause hybridization of the nucleic acid analyte with the functionalized probe. The cooling component may then cool the sample to a temperature sufficient to cause any non-hybridized probe components (e.g. free donor and quencher strands) to rehybridize with one another. The nucleic acid detection complexes are bound to a plurality of functionalized particles in a fluid sample (block 604). The particles may be functionalized with a binding agent complimentary to a binding agent associated with the functionalized probe. The functionalized particles having the nucleic acid detection complexes bound thereto are then separated from the fluid sample using a density media (block 606). Separation may occur by spinning the microfluidic disk and creating a centrifugal force which drives the particles having nucleic acid detection complexes bound thereto through the density media while the fluid sample remains outside of the density media. The nucleic acid analyte within the complex can be detected by detecting a signal emitted by the detection agent (block 608). The signal may be detected using a detection module as previously discussed and quantified to evaluate the presence of a nucleic acid analyte within the sample.

Figure 7:
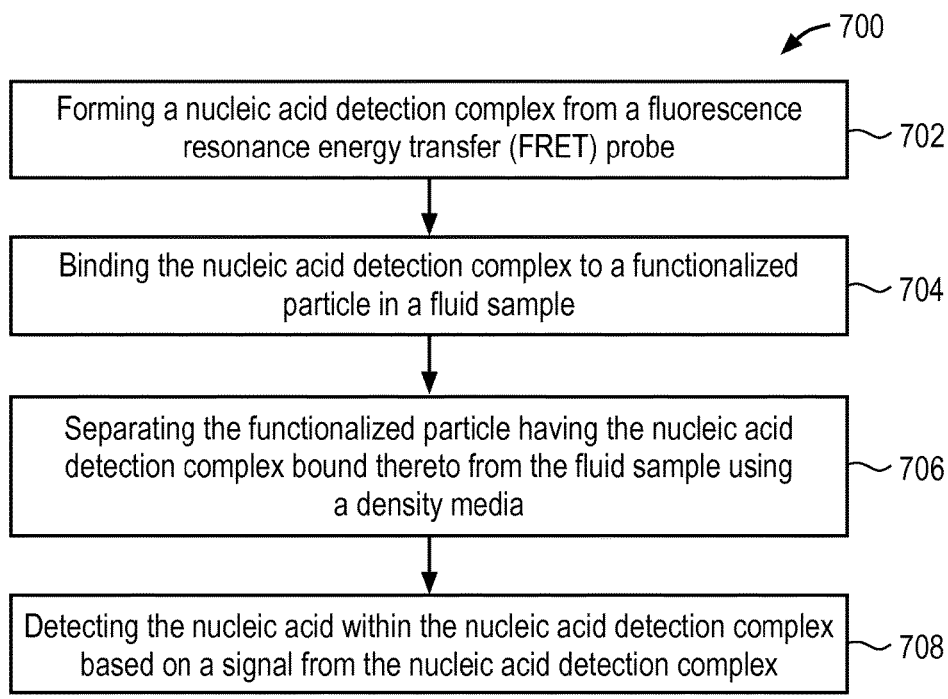
FIG. 7 illustrates a flow diagram of one embodiment of a process for detecting a nucleic acid analyte.

FIG. 7 illustrates a flow diagram of another embodiment of a process for detecting a nucleic acid analyte. Process 700 may include forming a nucleic acid detection complex from a Förster resonance energy transfer (FRET) probe (block 702). Representatively, the complex may be formed by melting a quencher strand off of a donor strand in the presence of the target analyte such that the analyte can than hybridize to the donor strand. The complex may then be bound to a functionalized particle (e.g., a streptavidin-conjugated particle) in a fluid sample (block 704). The functionalized particle having the complex bound thereto may be separated from the fluid sample using a density media (block 706). The nucleic acid within the complex may be detected by detecting a signal of the detecting agent within the complex (block 708).

It is noted that the techniques described herein significantly reduce assay time as compared to conventional techniques for quantifying pathogens and other nucleic acid analytes because they do not require the tedious amplification steps typically used. Rather, the complexes including the target analyte and detection agent, are concentrated onto carriers which are then reduced to a pellet form, thus eliminating the need for amplification of the signal through thermocycling and secondary antibodies.

While certain embodiments have been described and shown in the accompanying drawings, it is to be understood that such embodiments are merely illustrative of and not restrictive on the broad invention, and that the invention is not limited to the specific constructions and arrangements shown and described, since various other modifications may occur to those of ordinary skill in the art. The description is thus to be regarded as illustrative instead of limiting.

What is claimed is:

1. A method for detection of a nucleic acid using a microfluidic disk, the method comprising:
   introducing a fluorescence resonance energy transfer (FRET) probe to a mixing chamber within a microfluidic disk, wherein the mixing chamber is fluidly coupled to a detection chamber, and the microfluidic disk comprises a heating element;
   forming a nucleic acid detection complex from the FRET probe by heating the FRET probe and a target analyte within the mixing chamber and hybridizing the target analyte to a donor strand of the FRET probe;
   introducing a functionalized particle and a fluid sample into the mixing chamber and binding the nucleic acid detection complex to the functionalized particle in the fluid sample;
   separating the functionalized particle having the nucleic acid detection complex bound thereto from the fluid sample within a detection chamber of the microfluidic disk, wherein separating comprises introducing a density media into the detection chamber, and applying a centrifugal force to drive the functionalized particle having the nucleic acid detection complex bound thereto through the density media, wherein the density media is a solution comprising dextran in an amount of 7% dissolved in a physiological salt solution comprising 2-[2-[3,4-bis(2-hydroxyethoxy)oxolan-2-yl]-2-(2-hydroxyethoxy)ethoxy]ethyl dodecanoate in an amount of 0.05%; and
   after separating, detecting the target analyte within the nucleic acid detection complex based on a signal from the nucleic acid detection complex.

2. The method of claim 1, wherein the donor strand is a functionalized donor strand from the FRET probe, and the FRET probe is synthesized against a listeriolysin O gene of *L. monocytogenes*.

3. The method of claim 2, wherein the nucleic acid analyte comprises a synthetic DNA.

4. The method of claim 2, wherein the functionalized donor strand comprises a biotinylated donor strand.

5. The method of claim 1, wherein the FRET probe further comprises a quencher strand having a DNA sequence between 12 bases and 25 bases in length, and
   forming the plurality of nucleic acid detection complexes comprises:
   heating the FRET probe to a temperature above a melting temperature of the donor strand and the quencher strand in the presence of the nucleic acid analyte to separate the donor strand from the quencher strand.

6. The method of claim 1, wherein the nucleic acid detection complex is a first nucleic acid detection complex, the method further comprising:
   binding a second nucleic acid detection complex to the functionalized particle.

7. The method of claim 1, wherein binding comprises:
   incubating the nucleic acid detection complex with the functionalized particle in the mixing chamber such that a binding agent of the functionalized probe binds with a binding agent of the functionalized particle.

8. The method of claim 1, wherein the centrifugal force is sufficient to drive the functionalized particle having the nucleic acid detection complex bound thereto through the density medium while the fluid sample remains outside of the density media.

9. A method for detection of a nucleic acid using a microfluidic disk, the method comprising:
   introducing a fluorescence resonance energy transfer (FRET) probe to a mixing chamber within a microfluidic disk, wherein the FRET probe is synthesized against a listeriolysin O gene of *L. monocytogenes*, and wherein the mixing chamber is fluidly coupled to a detection chamber, and the microfluidic disk comprises a heating element;
   forming a nucleic acid detection complex from the FRET probe by heating the FRET probe and a target analyte within the mixing chamber and hybridizing the target analyte to a donor strand of the FRET probe;
   introducing a functionalized particle and a fluid sample into the mixing chamber and binding the nucleic acid detection complex to the functionalized particle in the fluid sample;
   separating the functionalized particle having the nucleic acid detection complex bound thereto from the fluid sample within a detection chamber of the microfluidic disk, wherein separating comprises introducing a density media into the detection chamber, and applying a centrifugal force to drive the functionalized particle having the nucleic acid detection complex bound thereto through the density media, wherein the density media is a solution comprising dextran in an amount of 7% dissolved in a physiological salt solution comprising 2-[2-[3,4-bis(2-hydroxyethoxy)oxolan-2-yl]-2-(2-hydroxyethoxy)ethoxy]ethyl dodecanoate in an amount of 0.05%; and
   after separating, detecting the target analyte within the nucleic acid detection complex based on a signal from the nucleic acid detection complex.

* * * * *